(12) United States Patent
Thomas et al.

(10) Patent No.: US 8,592,531 B2
(45) Date of Patent: Nov. 26, 2013

(54) PROSTHETIC DEVICES

(75) Inventors: David B. Thomas, Suwanee, GA (US);
Nikica Maljkovic, New Orleans, LA (US); Mohammad Jamal El-Hibri, Atlanta, GA (US); Timothy Schuler, New Orleans, LA (US); Todd S. Rushing, Clinton, MS (US); Roy L. Carter, San Ramon, CA (US)

(73) Assignee: Solvay Advanced Polymers, L.L.C., Alpharetta, GA (US)

( * ) Notice: Subject to any disclaimer, the term of this patent is extended or adjusted under 35 U.S.C. 154(b) by 371 days.

(21) Appl. No.: 12/676,989

(22) PCT Filed: Sep. 9, 2008

(86) PCT No.: PCT/EP2008/061948
§ 371 (c)(1),
(2), (4) Date: Apr. 21, 2010

(87) PCT Pub. No.: WO2009/034087
PCT Pub. Date: Mar. 19, 2009

(65) Prior Publication Data
US 2010/0222888 A1    Sep. 2, 2010

Related U.S. Application Data

(60) Provisional application No. 60/971,314, filed on Sep. 11, 2007, provisional application No. 60/971,934, filed on Sep. 13, 2007.

(51) Int. Cl.
*C08G 2/20* (2006.01)
*C08G 8/02* (2006.01)
*C08G 14/00* (2006.01)
*C08F 283/00* (2006.01)

(52) U.S. Cl.
USPC ............ 525/471; 525/534; 528/220; 128/898

(58) Field of Classification Search
USPC ............ 525/471, 535, 534; 128/898; 528/220
See application file for complete search history.

(56) References Cited

U.S. PATENT DOCUMENTS

| | | |
|---|---|---|
| 4,164,794 A | 8/1979 | Spector et al. |
| 4,351,069 A | 9/1982 | Ballintyn et al. |
| 5,064,439 A | 11/1991 | Chang et al. |
| 5,176,710 A | 1/1993 | Hahn et al. |

(Continued)

FOREIGN PATENT DOCUMENTS

| | | |
|---|---|---|
| BE | 1015402 A6 | 3/2005 |
| CN | 1582860 A | 2/2005 |

(Continued)

OTHER PUBLICATIONS

U.S. Appl. No. 12/061,442, NPL.*

(Continued)

*Primary Examiner* — Duc Truong
(74) *Attorney, Agent, or Firm* — Oblon, Spivak, McClelland, Maier & Neustadt, L.L.P.

(57) ABSTRACT

A prosthetic device made of a first specific type of polyarylene, taken alone or in combination with a second specific type of polyarylene, featuring some unexpected advantages such as a very high strength and stiffness, good elongation properties, high chemical resistance, good biocompatibility as well as an outstanding impact resistance.

12 Claims, 1 Drawing Sheet

(56) References Cited

U.S. PATENT DOCUMENTS

| | | | |
|---|---|---|---|
| 5,181,930 | A | 1/1993 | Dumbleton et al. |
| 5,219,363 | A | 6/1993 | Crowninshield et al. |
| 5,236,457 | A | 8/1993 | Devanathan |
| 5,370,696 | A | 12/1994 | Jamison et al. |
| 5,397,365 | A | 3/1995 | Trentacosta |
| 5,443,512 | A | 8/1995 | Parr et al. |
| 5,782,930 | A | 7/1998 | Lin et al. |
| 5,872,159 | A | 2/1999 | Cougoulic et al. |
| 5,886,130 | A | 3/1999 | Trimmer et al. |
| 6,585,755 | B2 | 7/2003 | Jackson et al. |
| 6,602,293 | B1 | 8/2003 | Biermann et al. |
| 7,419,714 | B1 | 9/2008 | Magerl et al. |
| 2002/0099449 | A1 | 7/2002 | Speitling |
| 2002/0107577 | A1 | 8/2002 | Storer et al. |
| 2002/0111691 | A1 | 8/2002 | Wang et al. |
| 2002/0115742 | A1 | 8/2002 | Trieu et al. |
| 2002/0120336 | A1 | 8/2002 | Santilli |
| 2002/0173850 | A1 | 11/2002 | Brodke et al. |
| 2003/0004563 | A1 | 1/2003 | Jackson et al. |
| 2003/0135275 | A1 | 7/2003 | Garcia et al. |
| 2003/0195327 | A1 | 10/2003 | King |
| 2004/0059356 | A1 | 3/2004 | Gingras |
| 2004/0158324 | A1 | 8/2004 | Lange |
| 2004/0249471 | A1 | 12/2004 | Bindseil et al. |
| 2005/0136764 | A1 | 6/2005 | Sherman et al. |
| 2005/0214492 | A1 | 9/2005 | Zhong et al. |
| 2005/0228498 | A1 | 10/2005 | Andres |
| 2006/0116774 | A1 | 6/2006 | Jones et al. |
| 2006/0200245 | A1 | 9/2006 | Trieu |
| 2006/0241759 | A1 | 10/2006 | Trieu |
| 2006/0247638 | A1 | 11/2006 | Trieu |
| 2009/0069511 | A1 | 3/2009 | Thomas et al. |

FOREIGN PATENT DOCUMENTS

| | | |
|---|---|---|
| CN | 1593356 A | 3/2005 |
| DE | 19728131 A1 | 1/1999 |
| DE | 19823737 A1 | 12/1999 |
| DE | 10256345 C1 | 12/2003 |
| EP | 0598450 A1 | 5/1994 |
| EP | 0761242 A1 | 3/1997 |
| EP | 1813292 A1 | 8/2007 |
| GB | 2259253 A | 3/1993 |
| GB | 2319962 A | 6/1998 |
| WO | WO 93/04099 A1 | 3/1993 |
| WO | WO 93/14055 A1 | 7/1993 |
| WO | WO 96/39455 A1 | 12/1996 |
| WO | WO02070031 A1 | 9/2002 |
| WO | WO02071959 A1 | 9/2002 |
| WO | WO2004004592 A1 | 1/2004 |
| WO | WO2005072374 A2 | 8/2005 |
| WO | WO2005096759 A2 | 10/2005 |
| WO | WO2006037078 A2 | 4/2006 |
| WO | WO2006039636 A2 | 4/2006 |
| WO | WO2006094988 A2 | 9/2006 |
| WO | WO 2007/101857 * | 3/2007 |
| WO | WO 2007/051307 A2 | 5/2007 |
| WO | WO 2007/101852 A2 | 9/2007 |
| WO | WO 2008/088826 A2 | 7/2008 |

OTHER PUBLICATIONS

U.S. Appl. No. 12/719,181, filed Mar. 8, 2010, Satchit Srinivasan et al.

U.S. Appl. No. 12/281,023, filed Aug. 28, 2008, David B. Thomas et al.

Morgan, Sarah E. et al. "Surface characterization of rigid rod polymers", Annual Technical Conference—Society of Plastics Engineers (2004), 62nd (vol. 2), pp. 1943-1947 ; 5 pgs.

Beevers A. "New self-reinforcing polymer is stronger and harder than any other", (2004) Plastics Industry News, 20040520, retrieved online via http://www.PWR.com on Aug. 9, 2007—currently retrievable on the Internet URL: http://www.prw.com/subscriber/archshow.html?id=11748&q=Parmax+2004#Szene_1; 2 pgs.

Ogando J. "Unreinforced plastics get stiffer", Design news (Nov. 6, 2006), vol. 61, (16), p. 57, currently retrievable on the Internet: URL: http://www.designnews.com/article/print/4890-Unreinforced_Plastics_Get_Stiffer.php; 3 pgs.

Solvay Advanced Polymers "PrimoSpire™ self-reinforced polyphenylene", 2007, Brochure PR-50497, 20070200; 4 pgs.

Mississippi Polymer Technologies "Parmax® self-reinforced polymers", Brochure, 2 pg. (no publication date).

Solvay Advanced Polymers, "Solvay Advanced Polymers launches Solviva™ Biomaterials available for use in implantable medical devices", Kunstoffe Show press release, Oct. 24, 2007 ; 3 pgs.

Randic M., "Aromaticity of Polycyclic Conjugated Hydrocarbons", Chemical Reviews (2003), vol. 103, pp. 3449-3605, American Chemical Society ; 157 pgs.

Weast R.C., "Definitive rules for nomenclature of organic chemistry", CRC Handbook of Chemistry and Physics, 64th edition, (1983-1984), pp. C1-C44, CRC Press Inc., Boca Raton, Florida ; 44 pgs.

MC Michael C., Solvay Advanced Polymers, Jul. 28, 2006, retrieved from the Internet on Nov. 23, 2009: URL: http://www.solvayadvancedpolymers.com/static/wma/pdf/9/0/3/5/Primospire%20PR250%20NT.pdf, XP002556969 ; 4 pgs.

Dijckstra D.J. et al., "Worm-like morphology of semi-rigid substituted poly(p-phenylene)", J. Material Science, 2007, vol. 42, pp. 3810-3815, DOI 10.1007/s10853-006-0426-8, Ed. Springer Science+Business Media, LLC ; 6 pgs.

Wang Y. et al., "Clinical report of cervical arthroplasty in management of spondylotic myelopathy in Chinese", Journal of Orthopaedic Surgery and Research 2006, 1:13 doi:10.1186/1749-799X-1-13, http://www.josr-online.com/content/1/1/13 ; 6 pgs.

Hyperdictionary,com, "Meaning of prosthetic, prosthesis, dentistry, orthodontic, orthodontics and prosthodontics", http://www.hyperdictionary.com/dictionary/, copyright 2000-2009 ; 6 pgs.

Schwartz M., "Collaborative research and development (CR&D) Delivery order 0023: Molecular simulation for material design limits", Nov. 2005, 59 pgs.

* cited by examiner

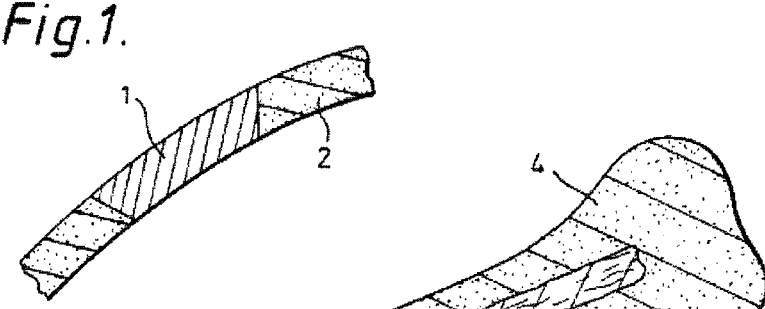
Fig.1.
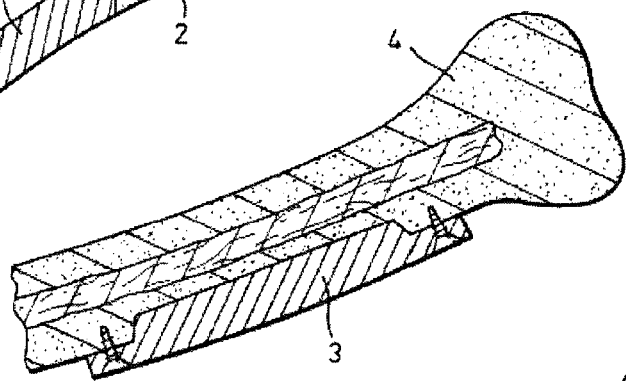
Fig.2.
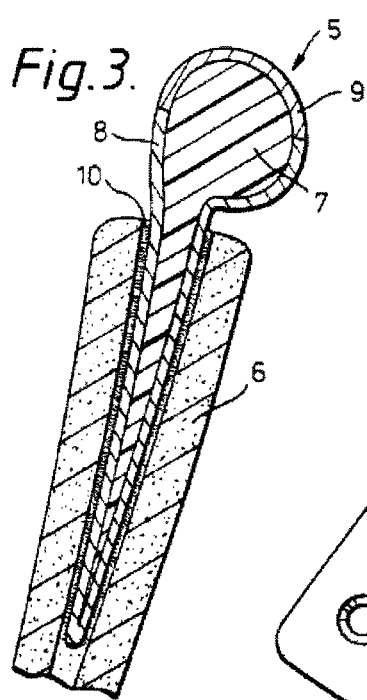
Fig.3.
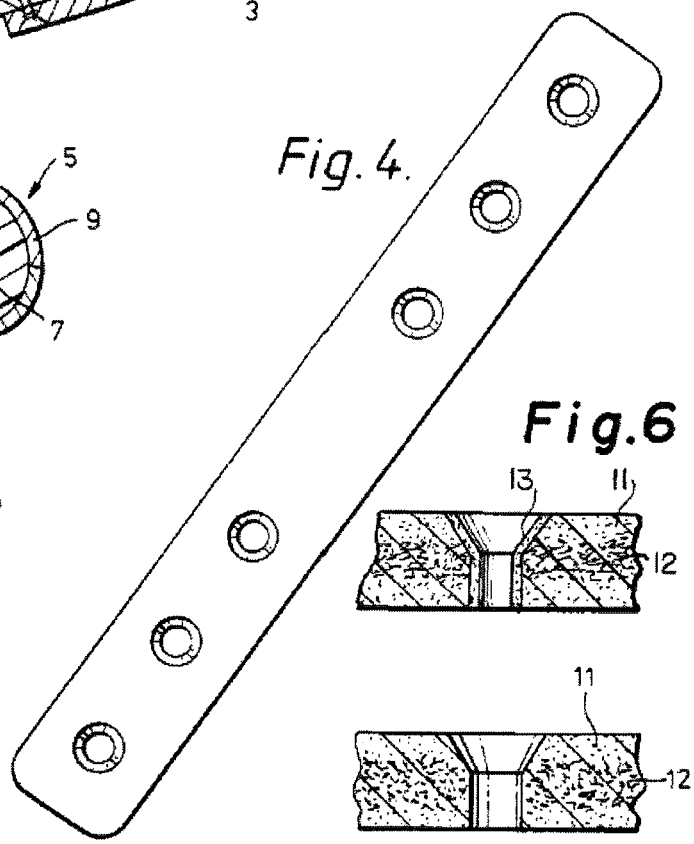
Fig.4.
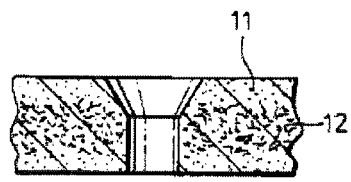
Fig.6
Fig.5.

PROSTHETIC DEVICES

CROSS-REFERENCE TO RELATED APPLICATIONS

This application is a U.S. national stage application under 35 U.S.C. §371 of International Application No. PCT/EP2008/061948 filed Sep. 9, 2008, which claims priority to and benefit under 35 U.S.C. §119(e) to U.S. provisional application No. 60/971,314 filed Sep. 11, 2007 and to U.S. provisional application No. 60/971,934 filed Sep. 13, 2007, the whole content of these applications being incorporated herein by reference for all purposes.

FIELD OF THE INVENTION

The present invention is related to a prosthetic device made of a first specific type of polyarylene, taken alone or in combination with a second specific type of polyarylene. Such prosthetic device features some unexpected advantages.

BACKGROUND OF THE INVENTION

Due both to demographic change and to developments in medical science; the number of surgical procedures involving prosthesis implantation is rising rapidly. The more obvious examples of prosthetic devices are hip or knee replacements and false teeth. Other less well-known examples are stems, heart valves, bone screws and plates and spinal fixators.

Prosthesis must be tolerated by the patient and not altered in time. Materials that may be suitable for each type of prosthesis are subjected to precise specifications. Indeed, if the prosthesis is a dental implant or a hip replacement the specifications will be very different. The most important requirements are mechanical properties similar to those of bone to allow the transfer constraints between bone and prosthesis, chemical resistance to corrosion, chemical inertia in relation to the environment and biocompatibility. These properties must be controlled to maintain the integrity of used materials. The human body is an aggressive and corrosive environment mainly because of concentrations of chloride ions (113 mEq/l in blood plasma and 117 mEq/l in the interstitial fluid, which is sufficient to corrode metallic materials) and dissolved oxygen. For dental implants, conditions are even tougher since the saliva contains more sulfur products that make it still more corrosive. The term "biocompatibility" is defined by the Dorland's Medical Dictionary as the quality of not having toxic or injurious effects on biological systems. This encompasses both the material and host responses to an implant. The host response to an implant can be highly complex and is often linked to the material response. It is also dependent on the anatomical position of the implant. For a material to be biocompatible, it should not elicit any adverse host reactions to its presence. Inflammation and encapsulation phenomena may occur when the prosthesis suffer from low biocompatibility.

Typically, prosthetic devices are made of inorganic (metal, alloys, ceramic and glass) and/or polymeric materials.

It is a fact that most pure metals and alloys are chemically unstable in many everyday environments due to their tendency to corrode. In the complex environment of the human body, metals and alloys are subject to electrochemical corrosion mechanisms, with bodily fluids acting as an electrolyte. While alloys such as stainless steel may appear to be highly stable and are widely used for kitchenware, eating utensils and jewelry, there are many situations that can cause severe corrosion of this material, and it is not the best choice for use in prosthetic devices.

Compared to inorganic materials, polymeric materials have certain advantages: they are lightweight, corrosion resistant, they can be directly shaped by molding and offer design freedoms. Over the past 4 years, the price of steel and non-ferrous metals grew faster than polymers and they require also less energy to be implemented. Among various existing polymers, only some of them have been used in the prosthesis industry so far, mainly because of their biocompatibility. Examples of such polymers are polymethyl methacrylate, polystyrene, poly(ether ether ketone) . . . .

Polyarylenes exhibit some outstanding performance properties, including exceptionally high strength, stiffness, hardness, scratch resistance, dimensional stability, great friction and wear properties, high solvent resistance and exceptional low temperature performance. These properties make them excellent candidates for end-use applications such as: mechanical components, aircraft interiors, coatings . . . .

In general, the so far known polyarylenes, while offering an exceptionally high level of strength and stiffness (which often even exceeds the needs of the applications wherein they are used) suffer irremediably from limitations in toughness-related properties:

they have limited elongability;
they have limited impact resistance (as typically characterized by standard notched and unnotched Izod tests).

They also have also limitations in melt processability due to their high viscosities, and tend to be anisotropic when melt fabricated under high shear such as during injection molding. Also, they have some limitations in chemical resistance.

All materials used in the prior art prosthetic devices and known to the Applicant still suffer from a limited impact resistance, which is a key property for such application where such materials are submitted to various and harsh conditions.

There remains thus a strong need for a prosthetic device presenting a superior balance of properties, including part or preferably all of the following ones:
  very high strength;
  very high stiffness;
  good elongation properties;
  good melt processability (in particular, good injection moldability);
  high chemical resistance;
  good biocompatibility;
  outstanding impact resistance, as possibly characterized by a standard no-notch IZOD test (ASTM D-4810).

In fact, there is a specific need to improve the mechanical properties of the existing prosthetic devices and in particular their impact resistance while at least maintaining their biocompatibility.

The Applicant has found that a first specific type of polyarylene, taken alone or in combination with a second specific type of polyarylene offer surprisingly and in particular a good biocompatibility and impact resistance. This outstanding property may be useful in certain demanding applications, such as articles used as prosthetic devices.

It has been surprisingly found that the materials comprising:
(i) at least one polyarylene (P2) of another specific type, characterized by a "high" amount of kink-forming arylene units (up to 100%) such as Primospire® PR-250 polyphenylene, and optionally;
(ii) at least one polyarylene (P1) of a first specific type, characterized by a "low" amount (down to 0%) of kink-forming arylene units such as Primospire® PR-120 polyphenylene (formerly Parmax® 1200); are characterized by very good impact resistance properties. The intended meaning of the terms "low" and "high" will become clear in the light of what follows.

These outstanding properties have already been described in EP2007/052095, the content of which is incorporated by reference, which illustrates some of the surprising behaviors related to these specific materials.

The present invention is thus related to a prosthetic device comprising at least one part consisting of a material comprising at least one polyarylene (P2), of which the efficient arylene recurring units (R2) are a mix (M2) consisting of:
  less than 70 mole %, down to 0 mole %, based on the total number of moles of efficient arylene recurring units (R2), of rigid rod-forming arylene units (Ra), said rigid rod-forming arylene units (Ra) being optionally substituted by at least one monovalent substituting group
with
  more than 30 mole %, up to 100 mole %, based on the total number of moles of efficient arylene recurring units (R2), of kink-forming arylene units (Rb), said kink-forming arylene units being optionally substituted by at least one monovalent substituting group.

The present invention is also related to a prosthetic device comprising at least one part consisting of a material comprising:
at least one polyarylene (P2), of which the efficient arylene recurring units (R2) are a mix (M2) consisting of:
  less than 70 mole %, down to 0 mole %, based on the total number of moles of efficient arylene recurring units (R2), of rigid rod-forming arylene units (Ra), said rigid rod-forming arylene units (Ra) being optionally substituted by at least one monovalent substituting group
with
  more than 30 mole %, up to 100 mole %, based on the total number of moles of efficient arylene recurring units (R2), of kink-forming arylene units (Rb), said kink-forming arylene units being optionally substituted by at least one monovalent substituting group.
and
at least one polyarylene (P1), of which the efficient arylene recurring units (R1) are a mix (M1) consisting of:
  from 70 mole % to 100 mole %, based on the total number of moles of efficient arylene recurring units (R1), of rigid rod-forming arylene units (Ra), said rigid rod-forming arylene units (Ra) being optionally substituted by at least one monovalent substituting group
with
  from 0 to 30 mole %, based on the total number of moles of efficient arylene recurring units (R1), of kink-forming arylene units (Rb), said kink-forming arylene units being optionally substituted by at least one monovalent substituting group.

The prosthetic devices of the present invention feature some unexpected advantages because of the materials of which they are made.

BRIEF DESCRIPTION OF THE FIGURES

Illustrated in sectional view in the drawings are,
in FIG. 1, a cranial plate 1 in situ within an aperture cut into the skull 2;
in FIG. 2 an insert 3 in a long bone 4 from which part of the bone had been removed;
and in FIG. 3 a femur head replacement 5 in situ within a femur 6. This last device comprises a core component 7 of a cement composition as described in European Patent Specification No. 21682 and comprising a surface coating of polyarylene (P2) and polyarylene (P1) 8, a bearing surface 9 of titanium and a fibrous surface layer 10.

A bone plate shown in perspective in FIG. 4 is shown also in enlarged section in FIG. 5, to illustrate the use of a polyarylene (P2) and polyarylene (P1) outer coating 11 upon a core region comprising a polyarylene (P2) and polyarylene (P1)-carbon fibre composite 12.

FIG. 6 shows the presence of polyarylene (P2) and polyarylene (P1) 13 also after refilling of the screw holes and redrilling.

DETAILED DESCRIPTION OF THE INVENTION

The Prosthetic Device

To the purposes of the invention, the term "prosthetic device" is intended to denote an artificial device which is made to replace and act as a missing biological structure. Prosthetic devices may have structural features which make them suitable to act as reinforcement or replacement of a missing or defective animal or human body part, e.g. a bone implant. Prosthetic devices of many shapes, configurations and properties are commonly employed within the living body. They can be used to replace parts lost by injury (traumatic or chirurgical) or missing from birth (congenital) or to supplement defective body parts.

For the sake of clarity, the term "part of a prosthetic device" is intended to denote a piece or portion which is combined with others to make up the whole prosthetic device. The external coating of a prosthetic device falls thus within this scope.

The prosthetic device of the present invention may comprise additional parts. Additional parts are intended to denote parts of the prosthetic devices which do not aim to replace a part of the body as such, but perform a supplementary function. For instance, it may comprise metal inserts, structural reinforcements, radio-opaque inserts, moving motor-driven assemblies, electronic devices, controlling units and the like.

The prosthetic device according to the present invention may be an orthopaedic prosthesis for building and/or repairing and/or improving surface properties of skeletal bones and joints such as, but not limited to ligaments, tendons, cartilage, bones, hip joints, knee prosthesis, spinal disc orthoprosthesis.

Orthopaedic prostheses comprise manufactured replacements for the ends and articulating surfaces of the bones of the skeleton. Such prostheses are generally implanted to repair or reconstruct all or part of an articulating skeletal joint that is functioning abnormally due to disease, trauma or congenital defect. Other forms of implantable orthopaedic prostheses, beyond providing manufactured replacements for the ends and articulating surfaces of the bones of the skeletal joints, also provide manufactured replacements for portions of the bones distant from the articulating surface. These other forms may be used in cases of abnormally extensive atrophy or resorption of bone in the vicinity of the articulating surface or prior implant, or in cases where an extensive amount of bone is to be intentionally resected to treat oncological or other diseases of the bone. Because the natural bony areas to which ligaments, tendons and other soft tissues attach are often lost to such extensive resections of the bone, implantable orthopaedic implants designed for such cases often include means for attaching bone and/or soft tissue directly to the implant. Generally such means also provide an initial mechanical attachment, supplemented by later ingrowth and ongrowth of the bone and soft tissue to the prosthesis.

Example of such prosthetic devices are described in many patent references, such as in U.S. Pat. No. 4,164,794A, U.S. Pat. No. 4,351,069A, U.S. Pat. No. 4,662,887A, U.S. Pat. No. 5,064,439A, U.S. Pat. No. 5,219,363A, U.S. Pat. No. 5,397,365A, U.S. Pat. No. 5,443,512A, U.S. Pat. No. 5,176,710A, U.S. Pat. No. 5,181,930A, GB 2,259,253A1, U.S. Pat. No. 5,370,696A, U.S. Pat. No. 5,236,457A, EP 0598450A1, U.S. Pat. No. 5,872,159A, EP 0761242A1, U.S. Pat. No. 5,782,930A, U.S. Pat. No. 6,602,293B, GB 2,319,962A1, DE 19728131A1, DE 19823737A1, US 2002107577A, US 2002111691A, WO 02070031A1, US 2002099449A, US 2002115742A, US 2002120336A, US2004158324A, WO 02071959A1, US 2002173850A, US 2003004563A, US 2003135275A, US 2003195327A, US 2004059356A, DE 10256345C1, BE 1015402AG, US 2004249471A, CN 1582860A, US 2005228498A, US 2005136764A, WO 05096759A2, CN 1593356A, WO 06039636A2, US 2006116774A, US 2006200245A, US 2006241759A, US 2006247638A, WO 07051307A2 and EP 1813292A, the whole content of all of them being herein incorporated by reference.

For example, the prosthetic device of the present invention may be selected from the group consisting of:
  orthopaedic prosthesis such as ligaments, tendons, cartilage, bones, hip joints, knee prosthesis, spinal disc orthoprosthesis;
  dental structures such as dentures, partial dentures;
  prosthetic structures for other body parts, such as prosthetic devices that serve as artificial body parts including limbs, eyes, implants, included cosmetic implants, hearing aids, and the like, such as spectacle frames;
  fixed prosthetic anatomical devices such as caps, crowns and other non-dental anatomical replacement structures.

The Polyarylenes (P1) and (P2)
Features Common to Polyarylenes (P1) and (P2)

For the sake of clarity, all the definitions and preferences expressed in the present chapter "Features common to polyarylenes (P1) and (P2)", whatever their concern and whatever the level of preference expressed, can be applied independently from each other to polyarylene (P1) and to polyarylene (P2).

For the purpose of the present invention, an arylene group is a hydrocarbon divalent group consisting of one core composed of one benzenic ring or of a plurality of benzenic rings fused together by sharing two or more neighboring ring carbon atoms, and of two ends.

Non limitative examples of arylene groups are phenylenes, naphthylenes, anthrylenes, phenanthrylenes, tetracenylenes, triphenylylenes, pyrenylenes, and perylenylenes. The arylene groups (especially the numbering of the ring carbon atoms) were named in accordance with the recommendations of the CRC Handbook of Chemistry and Physics, 64$^{th}$ edition, pages C1-C44, especially p. C11-C12.

Arylene groups present usually a certain level of aromaticity; for this reason, they are often reported as "aromatic" groups. The level of aromaticity of the arylene groups depends on the nature of the arylene group; as thoroughly explained in Chem. Rev. 2003, 103, 3449-3605, "Aromaticity of Polycyclic Conjugated Hydrocarbons", the level of aromaticity of a polycyclic aromatic hydrocarbon can be notably quantified by the "index of benzene character" B, as defined on p. 3531 of the same paper; values of B for a large set of polycyclic aromatic hydrocarbon are reported on table 40, same page.

An end of an arylene group is a free electron of a carbon atom contained in a (or the) benzenic ring of the arylene group, wherein an hydrogen atom linked to said carbon atom has been removed. Each end of an arylene group is capable of forming a linkage with another chemical group. An end of an arylene group, or more precisely the linkage capable of being formed by said end, can be characterized by a direction and by a sense; to the purpose of the present invention, the sense of the end of an arylene group is defined as going from the inside of the core of the arylene group to the outside of said core. As concerns more precisely arylene groups the ends of which have the same direction, such ends can be either of the same or opposite sense; also, their ends can be in the straight foregoing of each other, or not (otherwise said, they can be disjoint).

The polyarylenes (P1) and (P2) are polyarylenes, in that they are polymers of which more than 50 wt. % of the recurring units are efficient arylene recurring units, respectively named recurring (R1) [for the polyarylene (P1)] and (R2) [for the polyarylene (P2)].

Hereinafter, recurring units (R) denote indifferently recurring units (R1) or recurring units (R2). As already above stated, all the definitions and preferences expressed in the present chapter, whatever their concern and whatever the level of preference expressed, can be applied independently from each other to polyarylene (P1) and to polyarylene (P2); thus, in particular, all the definitions and preferences expressed in the present chapter regarding recurring units (R) can be applied independently from each other to recurring units (R1) and recurring units (R2).

Efficient arylene recurring units (R) are:
  arylene units, in that they are of one or more formulae consisting of an optionally substituted arylene group;
  efficient, in that said optionally substituted arylene group is linked by each of its two ends to two other optionally substituted arylene groups via a direct C—C linkage.

That the optionally substituted arylene group is linked by each of its two ends to two other optionally substituted arylene groups via a direct C—C linkage, is an essential feature of the efficient arylene recurring units (R). Thus, an arylene recurring unit which is linked by at least one of its two ends to a group other than an arylene group such as phenylene recurring units $\phi_1$, $\phi_2$ and $\phi_{2'}$ below:

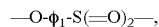

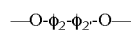

are not efficient arylene recurring units (R) in the sense of the present invention.

The arylene groups of which the efficient arylene recurring units (R) consist can be unsubstituted. Alternatively, they can be substituted by at least one monovalent substituting group.

The monovalent substituting group is usually not polymeric in nature; its molecular weight is preferably below 500, more preferably below 300, still more preferably below 200 and most preferably below 150.

Should the optionally substituted group be effectively substituted by at least one monovalent substituting group, said monovalent substituting group is advantageously a solubilizing group. A solubilizing group is one increasing the solubility of the polyarylene of concern in at least one organic solvent, in particular in at least one of dimethylformamide, N-methylpyrrolidinone, hexamethylphosphoric triamide, benzene, tetrahydrofuran and dimethoxyethane, which can be used as solvents during the synthesis of the polyarylene by a solution polymerization process.

The monovalent substituting group is also advantageously a group which increases the fusibility of the polyarylene, i.e.

it lowers its glass transition temperature and its melt viscosity, so as to desirably make the polyarylene suitable for thermoprocessing.

Preferably, the monovalent substituting group is chosen from:
- hydrocarbyls such as alkyls, aryls, alkylaryls and aralkyls;
- halogenos such as —Cl, —Br, —F and —I;
- hydrocarbyl groups partially or completely substituted by at least one halogen atom such as halogenoalkyls, halogenoaryls, halogenoalkylaryls and halogenoaralkyls;
- hydroxyl;
- hydrocarbyl groups substituted by at least one hydroxyl group, such as hydroxyalkyls, hydroxyaryls, hydroxyalkylaryls and hydroxyaralkyls;
- hydrocarbyloxys [—O—R, where R is a hydrocarbyl group], such as alkoxys, aryloxys, alkylaryloxys and aralkyloxys;
- amino (—NH$_2$);
- hydrocarbyl groups substituted by at least one amino group, such as aminoalkyls and aminoaryls;
- hydrocarbylamines [—NHR or —NR$_2$, where R is a hydrocarbyl group] such as alkylamines and arylamines;
- carboxylic acids and their metal or ammonium salts, carboxylic acid halides, carboxylic anhydrides;
- hydrocarbyl groups substituted by at least one of carboxylic acids, metals or ammonium salts thereof, carboxylic acid halides and carboxylic anhydrides, such as —R—C(=O)OH where R is an alkyl or an aryl group;
- hydrocarbylesters [—C(=O)OR or —O—C(=O)R, where R is a hydrocarbyl group] such as alkylesters, arylesters, alkylarylesters and aralkylesters;
- amido [—C(=O)NH$_2$];
- hydrocarbyl groups substituted by at least one amido group;
- hydrocarbylamide monoesters [—C(=O)NHR or —NH—C(=O)—R, where R is a hydrocarbyl group], such as alkylamides, arylamides, alkylarylamides and aralkylamides, and hydrocarbylamide diesters [—C(=O)NR$_2$ or —N—C(=O)R$_2$, where R are a hydrocarbyl groups], such as dialkylamides and diarylamides;
- sulfinic acid (—SO$_2$H), sulfonic acid (—SO$_3$H), their metal or ammonium salts;
- hydrocarbylsulfones [—S(=O)$_2$—R, where R is the hydrocarbyl group], such as alkylsulfones, arylsulfones, alkylarylsulfones, aralkylsulfones;
- aldehyde [—C(=O)H] and haloformyls [—C(=O)X, wherein X is a halogen atom];
- hydrocarbylketones [—C(=O)—R, where R is a hydrocarbyl group], such as alkylketones, arylketones, alkylarylketones and aralkylketones;
- hydrocarbyloxyhydrocarbylketones [—C(=O)—R$^1$—O—R$^2$, where R$^1$ is a divalent hydrocarbon group such as an alkylene, an arylene, an alkylarylene or an aralkylene, preferably a C$_1$-C$_{18}$ alkylene, a phenylene, a phenylene group substituted by at least one alkyl group, or an alkylene group substituted by at least one phenyl group; and R$^2$ is a hydrocarbyl group, such as an alkyl, aryl, alkylaryl or aralkyl group], such as alkyloxyalkylketones, alkyloxyarylketones, alkyloxyalkylarylketones, alkyloxyaralkylketones, aryloxyalkylketones, aryloxyarylketones, aryloxyalkylarylketones and aryloxyaralkylketones;
- any of the above groups comprising at least one hydrocarbyl group or a divalent hydrocarbon group R$^1$, wherein said hydrocarbyl group or said R$^1$ is itself substituted by at least one of the above listed monovalent substituting groups, e.g. an arylketone —C(=O)—R, where R is an aryl group substituted by one hydroxyl group;

where:
- the hydrocarbyl groups contain preferably from 1 and 30 carbon atoms, more preferably from 1 to 12 carbon atoms and still more preferably from 1 to 6 carbon atoms;
- the alkyl groups contain preferably from 1 to 18 carbon atoms, and more preferably from 1 to 6 carbon atoms; very preferably, they are chosen from methyl, ethyl, n-propyl, isopropyl, n-butyl, isobutyl and tert-butyl;
- the aryl groups are defined as monovalent groups consisting of one end and one core composed of one benzenic ring (such the phenyl group) or of a plurality of benzenic rings directly linked to each other via a carbon-carbon linkage (such as the biphenyl group) or fused together by sharing two or more neighboring ring carbon atoms (such as the naphthyl groups), and wherein the ring carbon atoms are possibly substituted by at least one nitrogen, oxygen or sulfur atom; preferably, in the aryl groups, no ring carbon atom is substituted;
- the aryl groups contain preferably from 6 to 30 carbon atoms; more preferably, they are phenyl groups;
- the alkyl group which is contained in the alkylaryl groups meets the preferences of the alkyl groups as above expressed;
- the aryl group which is contained in the aralkyl groups meets the preferences of the aryl groups as above expressed.

More preferably, the monovalent substituting group is chosen from hydrocarbylketones [—C(=O)—R, where R is a hydrocarbyl group] and hydrocarbyloxyhydrocarbylketones [—C(=O)—R$^1$—O—R$^2$, where R$^1$ is a divalent hydrocarbon group and R$^2$ is a hydrocarbyl group], said hydrocarbylketones and hydrocarbyloxyhydrocarbylketones being unsubstituted or substituted by at least one of the above listed monovalent substituting groups.

Still more preferably, the monovalent substituting group is chosen from arylketones and aryloxyarylketones, said arylketones and aryloxyarylketones being unsubstituted or substituted by at least one of the above listed monovalent substituting groups.

Most preferably, the monovalent substituting group is an (unsubstituted) arylketone, in particular it is phenylketone [—C(=O)-phenyl].

The core of the optionally substituted arylene group of the efficient arylene recurring units (R), is composed of preferably at most 3, more preferably at most 2, and still more preferably at most one benzenic ring. Then, when the core of the optionally substituted arylene group of the efficient arylene recurring units (R) is composed of one benzenic ring, the efficient arylene recurring units (R) are of one or more formulae consisting of an optionally substituted phenylene group, provided said optionally substituted phenylene group is linked by each of its two ends to two other optionally substituted arylene groups via a direct C—C linkage.

As above explained, the optionally substituted arylene group of the efficient arylene recurring units (R) is linked by each of its two ends to two other optionally substituted arylene groups via a direct C—C linkage. Preferably, it is linked by each of its two ends to two other optionally substituted phenylene groups via a direct C—C linkage.

As also above explained, both ends of the optionally substituted arylene group of the efficient arylene recurring units (R) can be characterized notably by a direction and by a sense.

A first set of possible efficient arylene recurring units (R) is composed of optionally substituted arylene groups, the ends of which have the same direction, are of opposite sense, and are in the straight foregoing of each other

[hereafter, rigid rod-forming arylene units (Ra)].

As already explained for recurring units (R) in general, rigid rod-forming arylene units (Ra) are efficient, in that they are linked by each of their two ends to two other optionally substituted arylene groups via a direct C—C linkage.

Non limitative examples of optionally substituted arylene groups of which the rigid rod-forming arylene units (Ra) are composed, include:

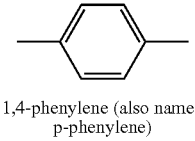
1,4-phenylene (also named p-phenylene)

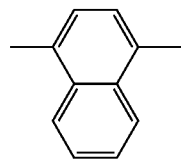
1,4-naphthylene

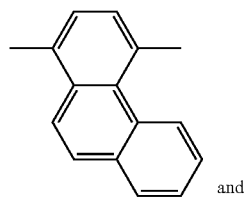
and

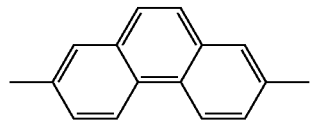
1,4-phenanthrylene and 2,7-phenanthrylene

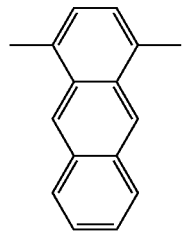
and
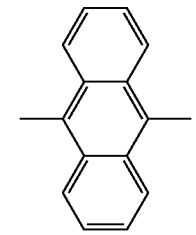
1,4-anthrylene and 9,10-anthrylene

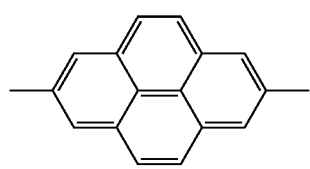
2,7-pyrenylene

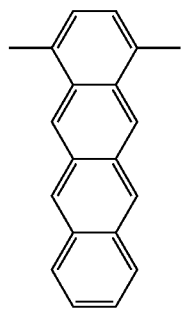
and
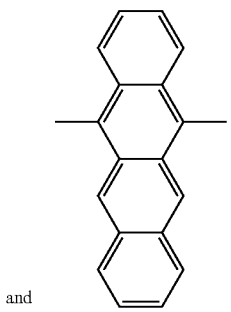
1,4-naphthacenylene and 5,12-naphthacenylene

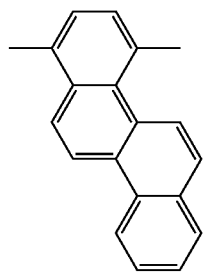
1,4-chrysenylene

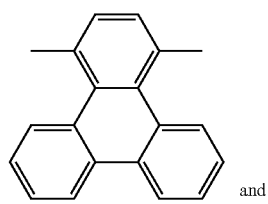
and

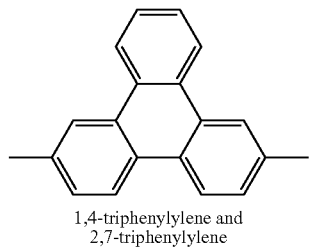
1,4-triphenylylene and 2,7-triphenylylene

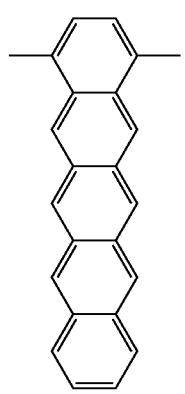
,
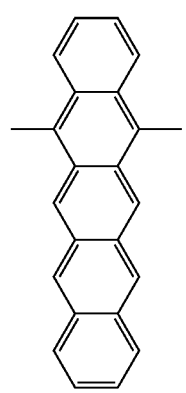
and

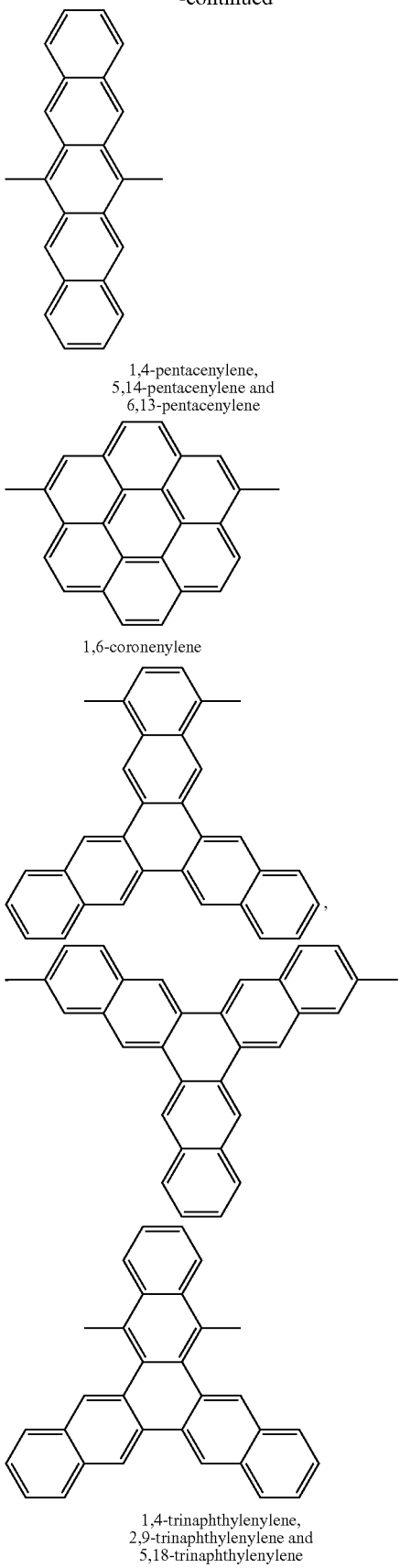

1,4-pentacenylene, 5,14-pentacenylene and 6,13-pentacenylene 1,6-coronenylene and 1,4-trinaphthylenylene, 2,9-trinaphthylenylene and 5,18-trinaphthylenylene and any of these groups substituted by at least one monovalent substituting group, as above defined, in particular by a phenylketone group.

Optionally substituted p-phenylenes are preferred as rigid rod-forming arylene units (Ra).

The above expressed definitions and preferences for recurring units (Ra) can be applied indifferently from each other to recurring units (Ra) possibly contained in the polyarylene (P1) as recurring units (R1), and to recurring units (Ra) possibly contained in the polyarylene (P2) as recurring units (R2).

Rigid rod-forming arylene units (Ra), when contained in the polyarylenes (P1) and (P2), result in straight polymer chains exhibiting an outstanding rigidity. For this reason, such polyarylenes are commonly referred to as "rigid-rod polymers".

A second set of possible efficient arylene recurring units (R) is composed of optionally substituted arylene groups, the ends of which
- either have a different direction, forming thus together an angle between 0 and 180°, said angle being possibly acute or obtuse,
- or have the same direction and the same sense,
- or have the same direction, are of opposite sense and are disjoint (i.e. not in the straight foregoing of each other)
[globally hereafter referred to as kink-forming arylene units (Rb)].

As above explained for recurring units (R) in general, kink-forming arylene units (Rb) are efficient, in that they are linked by each of their two ends to two other optionally substituted arylene groups via a direct C—C linkage.

A first subset of possible kink-forming arylene units (Rb) is composed of optionally substituted arylene groups, the ends of which have a different direction, forming together an acute angle [kink-forming arylene units (Rb-1)]. Non limitative examples of optionally substituted arylene groups the ends of which have a direction different from each other, include:

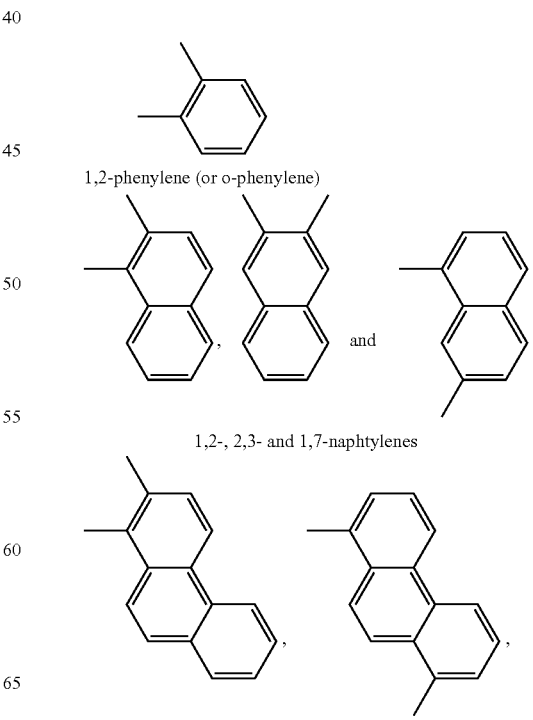

1,2-phenylene (or o-phenylene)

, and 1,2-, 2,3- and 1,7-naphtylenes

,   ,

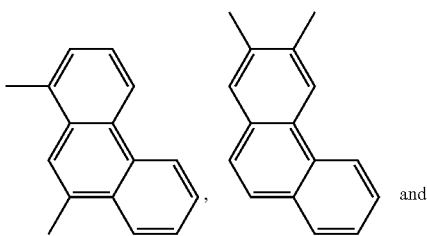

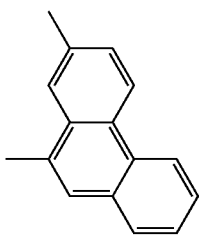

1,2-, 1,8-, 1,9-, 2,3-, 2,5- and 2,10- phenanthrylenes

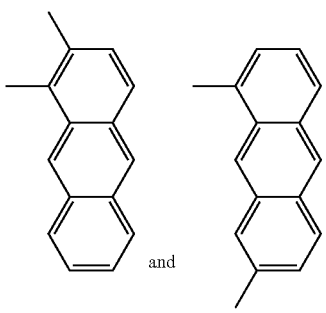

1,2- and 1,7- anthrylenes and any of these groups substituted by at least one monovalent substituting group, as above defined, in particular by a phenylketone group.

A second subset of possible kink-forming arylene units (Rb) is composed of optionally substituted arylene groups, the ends of which have a different direction, forming together an obtuse angle [kink-forming units (Rb-2)]. Non limitative examples of optionally substituted arylene groups the ends of which have a direction different from each other, include:

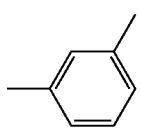

1,3-phenylene (or m-phenylene)

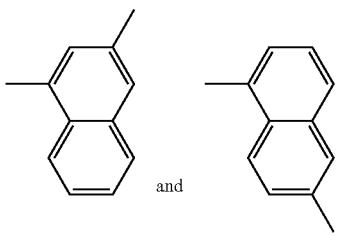

1,3- and 1,6-naphtylenes

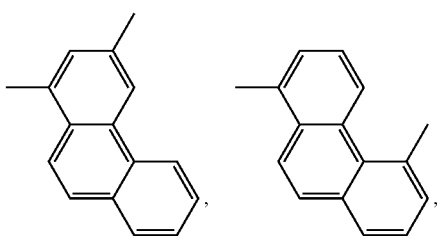

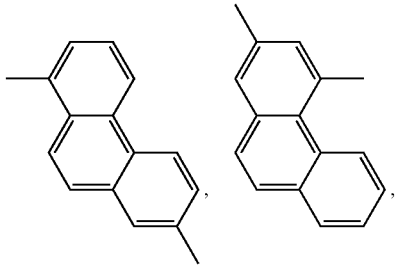

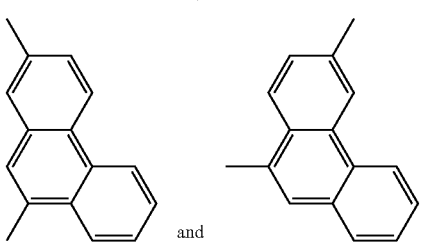

and 1,3-, 1,5-, 1,7-, 2,4-, 2,9- and 3,10-phenanthrylenes

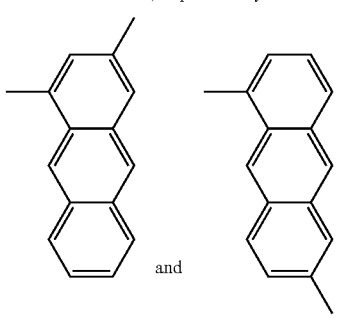

and 1,3- and 1,6-anthrylenes and any of these groups substituted by at least one monovalent substituting group, as above defined, in particular by a phenylketone group.

A third subset of possible kink-forming arylene units (Rb) is composed of optionally substituted arylene groups, the ends of which have the same direction and the same sense [kink-forming arylene units (Rb-3)]. Non limitative examples of optionally substituted arylene groups the ends of which the same direction and the same sense include:

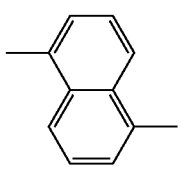

1,8-naphthylene

-continued

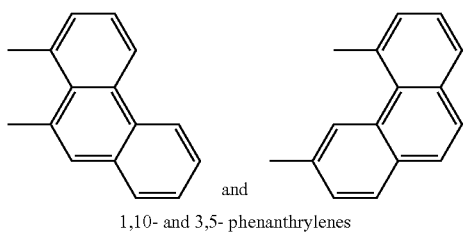
1,10- and 3,5- phenanthrylenes

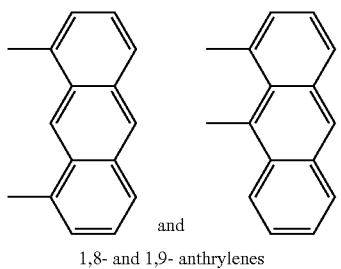
1,8- and 1,9- anthrylenes and any of these groups substituted by at least one monovalent substituting group, as above defined, in particular by a phenylketone group.

A fourth subset of possible kink-forming arylene units (Rb) is composed of optionally substituted arylene groups, the ends of which have the same direction, are of opposite sense and are disjoint [kink-forming arylene units (Rb-4)]. Non limitative examples of such optionally substituted arylene groups include:

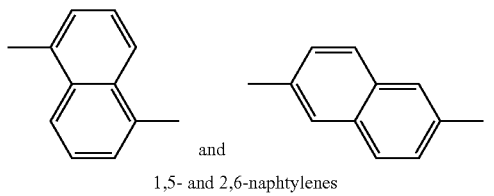
1,5- and 2,6-naphtylenes

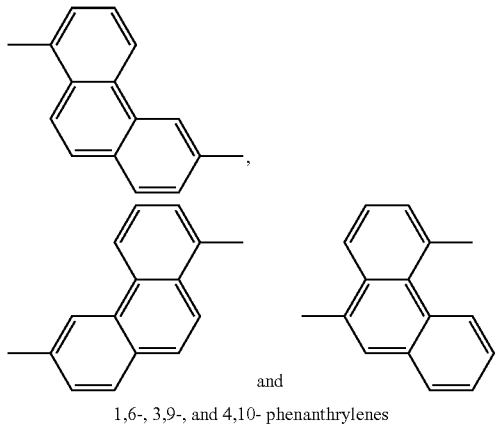
1,6-, 3,9-, and 4,10- phenanthrylenes

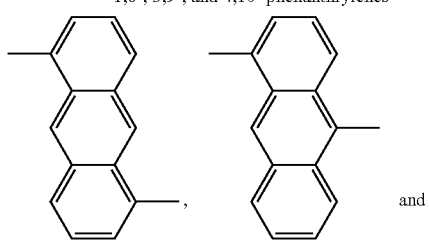

-continued

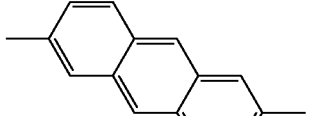
1,5-, 1,10-, and 2,6- anthrylenes and any of these groups substituted by at least one monovalent substituting group, as above defined, in particular by a phenylketone group.

Preferably, kink-forming arylene units (Rb) are chosen from kink-forming arylene units (Rb-1), kink-forming arylene units (Rb-2) and kink-forming arylene units (Rb-4). More preferably, kink-forming arylene units (Rb) are chosen from kink-forming arylene units (Rb-1) and kink-forming arylene units (Rb-2). Still more preferably, kink-forming arylene units (Rb) are chosen from kink-forming arylene units (Rb-1). Even still more preferably, kink-forming arylene units (Rb) are optionally substituted m-phenylenes.

The above expressed definitions and preferences for recurring units (Rb) and its variations (Rb-1), (Rb-2), (Rb-3) and (Rb-4), can be applied indifferently from each other to recurring units (Rb) possibly contained in the polyarylene (P1) as recurring units (R1), and to recurring units (Rb) possibly contained in the polyarylene (P2) as recurring units (R2).

Kink-forming arylene units (Rb), when contained in the polyarylenes (P1) and (P2), result in more or less kinked polymer chains, exhibiting a higher solubility and fusibility than straight polymer chains. For this reason, such polyarylenes are commonly referred to as "kinked polymers".

The polyarylenes (P1) and (P2) may further comprise recurring units (R*), different from efficient arylene recurring units (R).

Recurring units (R*) may contain or not at least one strong divalent electron withdrawing group linked on each of its ends to an arylene group. Non limitative examples of recurring units (R*) free of such strong divalent electron withdrawing group are:

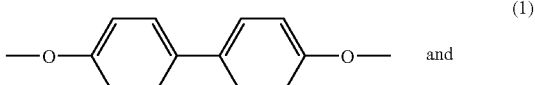 and (1)

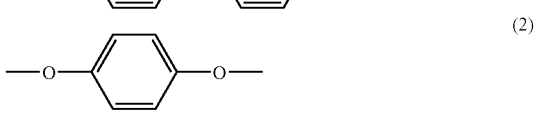 (2)

Recurring units (R*) contain preferably at least one strong divalent electron withdrawing group linked on each of its ends to an arylene group, in particular a p-phenylene group. The divalent electron withdrawing group is preferably chosen from the sulfone group [—S(═O)$_2$—], the carbonyl group [—C(═O)—], the vinylene group [—CH═CH—], the sulfoxide group [—S(═O)—], the azo group [—N═N—], saturated fluorocarbon groups like —C(CF$_3$)$_2$—, organic phosphine oxide groups [—P(═O)(═R$_h$)—, where R$_h$ is a hydrocarbyl group] and the ethylidene group [—C(═CA$_2$)—, where A can be hydrogen or halogen]. More preferably, the divalent electron withdrawing group is chosen from the sulfone group and the carbonyl group. Still more preferably, recurring units (R*) are chosen from:

(i) recurring units of formula

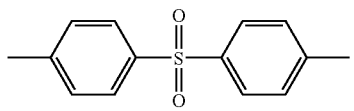
(3)

(ii) recurring units of formula

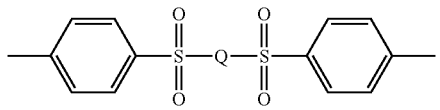
(4)

wherein Q is a group chosen from

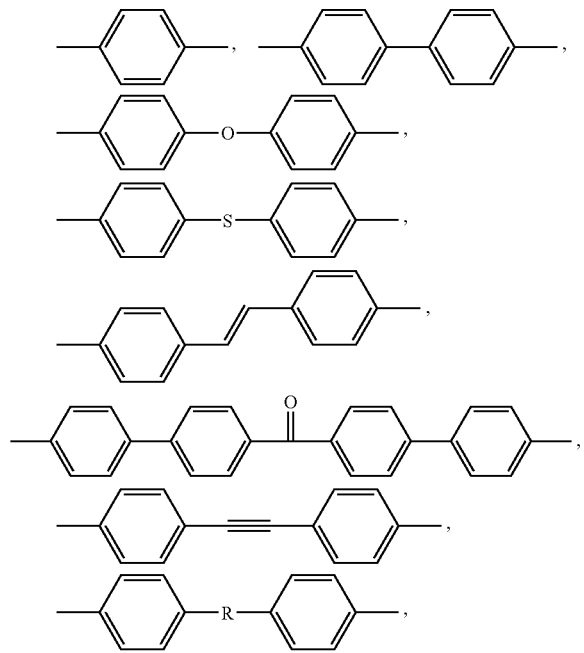

with R being:

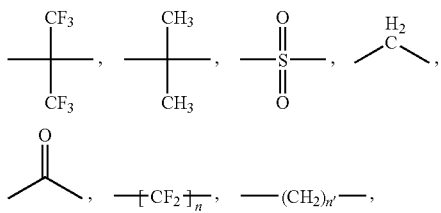

with n being an integer from 1 to 6 and n' being an integer from 2 to 6, Q being preferably chosen from

 and

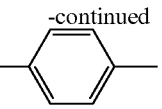

(iii) recurring units of formula

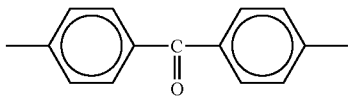
(5)

(iv) recurring units of formula

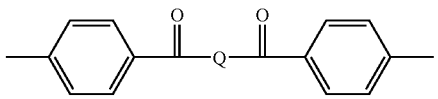
(6)

wherein Q is as above defined.

Preferably more than 75 wt. % and more preferably more than 90 wt. % of the recurring units of the polyarylenes (P1) and (P2) are efficient arylene recurring units (R). Still more preferably, essentially all, if not all, the recurring units of the polyarylenes (P1) and (P2) are efficient arylene recurring units (R).

The polyarylenes (P1) and (P2) have a number average molecular weight of advantageously greater than 1000, preferably greater than 5000, more preferably greater than about 10000 and still more preferably greater than 15000. On the other hand, the number average molecular weight of the polyarylenes (P1) and (P2) is usually below 100000, and preferably below 70000. The number average molecular weight of the polyarylenes (P1) and (P2) may be above 35000; alternatively, it may be of at most 35000, 25000 or 20000. The number average molecular weight of a polyarylene, in particular that of the polyarylenes (P1) and (P2), is advantageously determined by: (1) measuring a "relative" number average molecular weight of the polyarylene of concern by Gel Permeation Chromatography (GPC) using polystyrene calibration standards, then (2) dividing the so-measured "relative" number average molecular weight by a factor 2. It is proceeded accordingly because the skilled in the art who is a specialist of polyarylenes knows that their "relative" number average molecular weight, as measured by GPC, are generally off by a factor of about 2 times; it has already been accounted for this correction factor in all the above cited lower and upper limits of molecular weight.

They can be amorphous (i.e. it has no melting point) or semi-crystalline (i.e. it has a melting point). They are preferably amorphous.

They have a glass transition temperature of advantageously above 50° C., preferably above 120° C. and more preferably above 150° C.

The polyarylenes (P1) and (P2) can be prepared by any method. A method well known in the art to prepare them comprises polymerizing, preferably by reductive coupling, (i) at least one dihaloarylene molecular compound consisting of an optionally substituted rigid rod-forming arylene group, which is linked on each of its two ends to one halogen atom, such as chlorine, bromine and iodine, with (ii) at least one dihaloarylene molecular compounds consisting of an optionally substituted kink-forming arylene group, which is linked on each of its two ends to one halogen atom, such as chlorine, bromine, iodine, and fluorine. The elimination of the halogen atoms from the dihaloarylene molecular compounds results in the formation of respectively optionally substituted rigid rod-forming and optionally substituted kink-forming arylene groups.

Thus, for example:
the elimination of both chlorine atoms from a molecule of p-dichlorobenzene, p-dichlorobiphenyl or their homologous of general formula Cl-$(\phi)_N$-Cl, N being an integer from 3 to 10, results in the formation of respectively 1, 2 or N adjacent p-phenylene units (rigid rod-forming arylene units); thus, p-dichlorobenzene, p-dichlorobiphenyl and their homologous of general formula Cl-$(\phi)_N$-Cl, N as above defined, can be polymerized, so as to form p-phenylene units;
2,5-dichlorobenzophenone (p-dichlorobenzophenone) can be polymerized, so as to form 1,4-(benzoylphenylene) units (also rigid rod-forming arylene units);
m-dichlorobenzene can be polymerized, so as to form m-phenylene units (kink-forming arylene units).

The combined weight of the polyarylene (P1) and of the polyarylene (P2), based on the total weight of the material, is advantageously above 25%, preferably above 50%, more preferably above 80%, and still more preferably above 95%. Excellent results were obtained when the material consisted essentially of, or even consisted of, the polyarylene (P1) and the polyarylene (P2).

Features Specific to the Polyarylene (P1)

The efficient arylene recurring units (R1) of the polyarylene (P1) must be of a very specific type, namely they must be a mix (M1) consisting of:
from 70 mole % to 100 mole %, based on the total number of moles of efficient arylene recurring units (R1), of rigid rod-forming arylene units (Ra), said rigid rod-forming arylene units (Ra) being optionally substituted by at least one monovalent substituting group
with
from 0 to 30 mole %, based on the total number of moles of efficient arylene recurring units (R1), of kink-forming arylene units (Rb), said kink-forming arylene units being optionally substituted by at least one monovalent substituting group.

In the mix (M1), the number of moles of the kink-forming arylene units (Rb), based on the total number of moles of the efficient arylene recurring units (R1), is preferably of at least 1.0%, more preferably at least 5% and still more preferably at least 10%. On the other hand, in the mix (M1), the number of moles of the kink-forming arylene units (Rb), based on the total number of moles of the efficient arylene recurring units (R1), is preferably of at most 25%, more preferably at most 21%, still more preferably at most 18%.

Good results were obtained when the efficient arylene recurring units (R1) of the polyarylene (P1) were a mix (M1) consisting of p-phenylene units substituted by a phenylketone group with unsubstituted m-phenylene units, in a mole ratio of about 85:15.

Good results were also obtained when the polyarylene (P1) was a kinked rigid-rod polyphenylene copolymer, essentially all, if not all, the recurring units of which consisted of a mix (M1) of p-phenylene substituted by a phenylketone group with unsubstituted m-phenylene in a mole ratio p-phenylene: m-phenylene of from 75:25 to 99.0:1.0, preferably of from 79:21 to 95:5, more preferably of from 82:18 to 90:10, and still more preferably of about 85:15. Such a kinked rigid-rod polyphenylene copolymer is commercially available from Solvay Advanced Polymers, L.L.C. as PRIMOSPIRE® PR-120 polyphenylene.

The weight of the polyarylene (P1), based on the total weight of the material, is advantageously of at least 1%, preferably of at least 5%, more preferably of at least 10% and still more preferably of at least 15%. On the other hand, the weight of the polyarylene (P1), based on the total weight of the material, is advantageously of at most 99%, preferably of at most 95%, more preferably of at most 75% and still more preferably of at most 60%.

In a certain particular embodiment of the present invention (Emb-A1), the weight of the polyarylene (P1), based on the total weight of the material, is of at least 35%, and ranges preferably from 35 to 60%. In a certain other particular embodiment of the present invention (Emb-B1), the weight of the polyarylene (P1), based on the total weight of the material, is below 35%, and ranges preferably between 35%, down to 15%.

In the present invention, one, two, three, or even more than three different polyarylenes (P1) can be used.

Features Specific to the Polyarylene (P2)

The efficient arylene recurring units (R2) of the polyarylene (P2) must be of a very specific type, namely they must be a mix (M2) consisting of:
less than 70 mole %, down to 0 mole %, based on the total number of moles of efficient arylene recurring units (R2), of rigid rod-forming arylene units (Ra), said rigid rod-forming arylene units (Ra) being optionally substituted by at least one monovalent substituting group
with
more than 30 mole %, up to 100 mole %, based on the total number of moles of efficient arylene recurring units (R2), of kink-forming arylene units (Rb), said kink-forming arylene units being optionally substituted by at least one monovalent substituting group.

In the mix (M2), the number of moles of the kink-forming arylene units (Rb), based on the total number of moles of the efficient arylene recurring units (R2), is preferably of at least 35%, more preferably at least 40% and still more preferably at least 45%. On the other hand, in the mix (M2), the number of moles of the kink-forming arylene units (Rb), based on the total number of moles of the efficient arylene recurring units (R2), is preferably of at most 90%, more preferably at most 75%, still more preferably at most 65% and most preferably at most 55%.

Good results were obtained when the efficient arylene recurring units (R2) of the polyarylene (P2) were a mix (M2) consisting of p-phenylene units substituted by a phenylketone group with unsubstituted m-phenylene units, in a mole ratio of about 50:50.

Good results were also obtained when the polyarylene (P2) was a kinked rigid-rod polyphenylene copolymer, essentially all, if not all, the recurring units of which consisted of a mix (M2) of p-phenylene substituted by a phenylketone group with unsubstituted m-phenylene in a mole ratio p-phenylene: m-phenylene of from 25:75 to 65:35, preferably of from 35:65 to 60:40, more preferably of from 45:55 to 55:45, and still more preferably of about 50:50. Such a kinked rigid-rod polyphenylene copolymer is commercially available from Solvay Advanced Polymers, L.L.C. as PRIMOSPIRE® PR-250 polyphenylene.

The weight of the polyarylene (P2), based on the total weight of the material, is advantageously of at least 1%, preferably of at least 5%, more preferably of at least 25% and still more preferably of at least 40%. On the other hand, the weight of the polyarylene (P2), based on the total weight of the material, is advantageously of at most 99%, preferably of at most 95%, more preferably of at most 90% and still more preferably of at most 85%.

In a certain particular embodiment of the present invention [(Emb-A2), which is preferably the same embodiment as (Emb-A1), referred to in the chapter related to polyarylene (P1)], the weight of the polyarylene (P2), based on the total weight of the material, is of at most 65%, and ranges preferably from 40 to 65%. In a certain other particular embodiment of the present invention [(Emb-B2), which is preferably the same embodiment as (Emb-B1), referred to in the chapter related to polyarylene (P1)], the weight of the polyarylene (P2), based on the total weight of the material, is above 65%, and ranges preferably between 65%, up to 85%.

The weight of the polyarylene (P2), based on the combined weight of the polyarylene (P1) and the polyarylene (P2), is advantageously of at least 1%, preferably of at least 5%, more preferably of at least 25% and still more preferably of at least 40%. On the other hand, the weight of the polyarylene (P2), based on the combined weight of the polyarylene (P1) and the polyarylene (P2), is advantageously of at most 99%, preferably of at most 95%, more preferably of at most 90% and still more preferably of at most 85%.

In a certain particular embodiment of the present invention, the weight of the polyarylene (P2), based on the combined weight of the polyarylene (P1) and the polyarylene (P2), is of at most 65%, and ranges preferably from 40 to 65%. In a certain other particular embodiment of the present invention, the weight of the polyarylene (P2), based on the combined weight of the polyarylene (P1) and the polyarylene (P2), is above 65%, and ranges preferably between 65%, up to 85%.

In the present invention, one, two, three, or even more than three different polyarylenes (P2) can be used.

In a second embodiment, the prosthetic device according to the present invention comprising at least one part consisting of a material further comprises at least one polyarylene (P1).

In a preferred embodiment, the prosthetic devices of the present invention are made of a material comprising high purity polyarylene (P2). When the material further comprises polyarylene (P1), high purity polyarylene (P1) is also preferred. A high purity polyarylene is intended to denote a polyarylene featuring a purity of above 95%, preferably 98% and more preferably 99%.

Typical polyarylene contaminants are Ni, Zn and P.

High purity polyarylenes (P1) and (P2) contain advantageously less than 10 ppm of Ni, preferably less than 9 ppm, more preferably less than 8 ppm, still more preferably less than 6 ppm and most preferably less than 2 ppm Ni.

High purity polyarylenes (P1) and (P2) contain advantageously less than 200 ppm of Zn, preferably less than 150 ppm, more preferably less than 100 ppm, still more preferably less than 80 ppm and most preferably less than 50 ppm Zn.

High purity polyarylenes (P1) and (P2) contain advantageously less than 1000 ppm of P, preferably less than 800 ppm, more preferably less than 700 ppm, still more preferably less than 600 ppm and most preferably less than 500 ppm P.

High purity polyarylenes (P1) and (P2) contain preferably at the same time less than 5 ppm Ni, less than 50 ppm Zn and less than 800 ppm P.

High purity polyarylenes may be obtained from prior art processes, such as the one described in WO93/04099, WO93/14055, WO96/39455, WO2005/072374, the content of which are herein incorporated by reference. Additional treatments are preferably further carried out to such processes, and the reaction mixture obtained after polymerization is preferably treated as follows. The reaction mixture is then precipitated in an anti-solvent and then the polymer is isolated. The polymer is then washed multiple times with the anti-solvent to extract the residual dissolved catalysts which are converted to the metal salts which are soluble in the anti-solvents. Examples of anti-solvents are ethanol, propanol, 2-butanone, acetone, methanol, isopropanol and mixtures thereof. Mixtures of these anti-solvents with water or acidic aqueous solutions gave also good results. Excellent results were obtained using acetone, methanol, isopropanol. Such specific washing treatment leads advantageously to the obtention of high purity polyarylenes comprising low quantities of residuals, which make them especially well suited for their use in medical applications and in particular for the manufacture of prosthetic devices. High purity polyarylenes (P1) and (P2) and combinations thereof feature excellent mechanical properties and a good biocompatibility which make them excellent candidates for medical applications.

Another object of the present invention is thus related to the use of high purity polyarylenes (P1) and (P2) in medical applications. High purity polyarylenes (P1) and (P2) and combinations thereof are especially well suited for the manufacture of medical application devices such as bone replacement applications, fibers and films for medical applications, fixation devices and medical instruments.

Optional Ingredients

The material described hereabove may further contain a variety of other polymers, additives, fillers, and the like, collectively called ingredients. Conventional ingredients of polyarylene compositions, include fibrous reinforcing agents, particulate fillers and nucleating agents such as talc and silica, adhesion promoters, compatibilizers, curing agents, lubricants, metal particles, mold release agents, organic and/or inorganic pigments like $TiO_2$ and carbon black, dyes, flame retardants, smoke-suppressing agents, heat stabilizers, antioxidants, UV absorbers, tougheners such as rubbers, plasticizers, anti-static agents, melt viscosity depressants such as liquid crystalline polymers and the like.

In a particular embodiment, the material further comprises a thermoplastic polymer selected from the group consisting of polyamides, polyimides, polyetherimides, polyamideimides, polyarylsulfones, polyphenylsulfones, polyetherketones, polyetheretherketones, polyetherketoneketones, polyarylene ethers, polyphenylene ethers, poly(2,6-dimethyl-1,4-phenylene ether), polyphenylene sulfides, polyethersulfones, polybenzimidazoles, polycarbonates, polyesters, polyolefins, poly(methyl pentene), polytetrafluoroethylene, polyethylene, polypropylene, liquid crystalline polymers, halogenated polymers, and mixtures thereof.

In another particular embodiment, the material further contains a fibrous reinforcing agent, in particular an inorganic fibrous reinforcing agent such as glass fiber or carbon fiber. Thus, in a certain particular embodiment, the material comprises from 10 to 50 wt. %, in particular from 20 to 30 wt. %, of a reinforcing agent (all percentages based on the total weight of the material); an example of such a material is one composed of 35 wt. % of a polyarylene (P1), 35 wt. % of polyarylene (P2) homopolymer and 30 wt. % of glass fiber.

In still another particular embodiment, the material further contains an additive capable of promoting the formation of a char layer when the material is in contact with the flames of a fire [hereinafter, "char promoter"]; without being bound by any theory, the char layer would protect the core of material, slowing down its degradation. The char promoter may be an organic compound, such as a phenoxy derivative; alternatively, it may be inorganic, such as an oxide, a salt, or a combination thereof. The char promoter is preferably a combination of one or more oxides and one or more salts. Besides, the char promoter is preferably composed of one or more oxides, salts or combinations thereof, of one or more elements of families 3 to 12 of the Periodic Table of the Elements, more preferably of one or more elements of families 6, 7 and 11, and still more preferably of one or more elements selected from the group of Cr, Mo, W, Mn, Cu and Ag. Excellent results in terms of fire resistance were obtained when using $CuCr_2O_4 \cdot MnO$ as the char promoter. $CuCr_2O_4 \cdot MnO$ is notably commercially available as Engelhard Meteor Plus 9875 Black brand pigment. In this particular embodiment, the material comprises generally between 0.01 and 10 wt. % of the char promoter, based on the total weight of the material. The char promoter amount is preferably of at least 0.1 wt. %, and very preferably of at least 0.2 wt. %; besides, it is preferably of at most 5 wt. %, and very preferably of at most 2 wt. %.

The weight of the optional ingredients, based on the total weight of the material, is advantageously below 75%, preferably below 50%, more preferably below 25% and still more preferably below 10%. Excellent results were obtained when the material was essentially free, or even was completely free, of said optional ingredients.

Embodiment (E*)

In still another a particular embodiment (E*), the material further comprises a poly(aryl ether sulfone), namely a polymer of which at least 5 wt. % of the recurring units are recurring units of one or more formulae comprising at least one arylene group, at least one ether group (—O—) and at least one sulfone group [—S(=O)$_2$—].

The poly(aryl ether sulfone) may be a poly(biphenyl ether sulfone), in particular a polyphenylsulfone. To the purpose of the present invention, a poly(biphenyl ether sulfone) is intended to denote polymer of which more than 50 wt. % of the recurring units are recurring units of one or more formulae containing at least one p-biphenylene group:

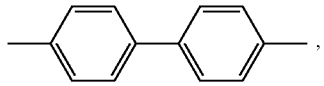

at least one ether group (—O—) and at least one sulfone group [—S(=O)$_2$—].

To the purpose of the present invention, a polyphenylsulfone is intended to denote any polymer of which more than 50 wt. % of the recurring units are recurring units:

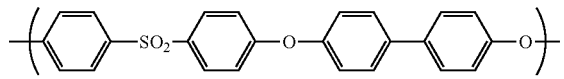

In embodiment (E*), the polyarylenes (P1) and (P2) may meet all the characteristics of the polyphenylenes described in WO2006/094988, the content of which is herein incorporated by reference, as long as they are compatible with those of respectively the polyarylenes (P1) and (P2) described in the present document.

The person skilled in the art will understand that the invention is not intended to be limited to this particular embodiment (E*), but encompasses also any embodiment other than (E*) which is described in the present document. Besides, various modifications to the embodiments described in the present document will be readily apparent to those skilled in the art, and the generic principles defined herein may be applied to other embodiments without departing from the spirit and scope of the invention; thus, this invention is also not intended to be limited to all the embodiments shown, but is to be accorded the widest scope consistent with the principles and features disclosed herein.

The material as described above, while offering an exceptionally high level of strength and stiffness (similar to that provided by PRIMOSPIRE® PR-120 and PRIMOSPIRE® PR-250 polyphenylenes), further provides at least one, preferably at least two and still more preferably all the following advantages:

the polymer material should have increased elongability; and/or the polymer material should have increased impact resistance; and/or the polymer material should have increased fire resistance.

which are illustrated in greater detail below by referring to the examples; however, the present invention is not limited to these examples.

EXAMPLES

Polyarylene (P1*) was used as polyarylene (P1). Polyarylene (P1*) is a kinked rigid-rod polyphenylene copolymer, essentially all, if not all, the recurring units of which consist of a mix of p-phenylene substituted by a phenylketone group with unsubstituted m-phenylene in a mole ratio p-phenylene:m-phenylene of about 85:15; it has a glass transition temperature of about 158° C. Such a kinked rigid-rod polyphenylene copolymer is commercially available from Solvay Advanced Polymers, L.L.C. as PRIMOSPIRE® PR-120 polyphenylene.

Polyarylene (P2*) was used as polyarylene (P2). Polyarylene (P2*) is a kinked rigid-rod polyphenylene copolymer, essentially all, if not all, the recurring units of which consist of a mix of p-phenylene substituted by a phenylketone group with unsubstituted m-phenylene in a mole ratio p-phenylene:m-phenylene of about 50:50; it has a glass transition temperature of about 165° C. Such a kinked rigid-rod polyphenylene copolymer is commercially available from Solvay Advanced Polymers, L.L.C. as PRIMOSPIRE® PR-250 polyphenylene.

Polyarylene compositions (E1), (E2), (E3) and (E4) comprising various proportions by weight of polyarylene (P2*) (and polyarylene (P1*)), were prepared by melt-mixing the polyarylene (P2*) (and the polyarylene (P1*)) using a Brabender Plasticorder.

Polyarylene compositions (E1), (E2), (E3) and (E4), as well as neat polyarylene control (P1*), were analyzed by standard physical testing methods. Processing conditions and physical properties are shown in Table 1.

Example 1

Flexural Properties

Flexural properties were determined according to ASTM D790.

Notched Izod impact strength values were determined according to ASTM D256.

Unnotched Izod impact strength values were determined according to ASTM D4812.

The results are reported in table 1.

TABLE 1

Flexural properties results

|  | (P1*) control | (E1) | (E2) | (E3) | (E4) |
|---|---|---|---|---|---|
| Polyarylene (P1*) (wt. %) | 100 | 95 | 50 | 5 | 0 |
| Polyarylene (P2*) (wt. %) | 0 | 5 | 50 | 95 | 100 |
| Conditions of preparation |  |  |  |  |  |
| Mixing temperature ° C. | 290 | 290 | 290 | 300 | 300 |
| Torque reading (gram force-meter) | 5000 | 4600 | 4150 | 2500 | 2300 |
| Flexural modulus (Mpsi) (ASTM D-790) | 1.12 | 1.1 | 1.01 | 0.89 | 0.86 |
| Flexural strength (Kpsi) (ASTM D-790) | 44.4 | 44.3 | 41.8 | 38.2 | 38.6 |
| Flexural elongation (%) (ASTM D-790) | 7.8 | 8.8 | 9.3 | 9.4 | 8.5 |

Surprisingly, polymer compositions (E1), (E2), (E3) and (E4), while offering an exceptionally high level of strength and stiffness (similar to that provided of PRIMOSPIRE® PR-120 and PRIMOSPIRE® PR-250 control (P1*)), further exhibited increased flexural elongation, in substantial progress with (P1*) control [synergistic behaviour].

Example 2

Impact Resistance Properties

The notched and unnotched impact resistance of polyarylene composition (E2) (according to the invention) and of control (P1*) was measured.

The results are reported in table 2.

TABLE 2

Impact resistance results

|  | (P1*) control | (E2) | (E4) |
|---|---|---|---|
| Polyarylene (P1*) (wt. %) | 100 | 50 | 0 |
| Polyarylene (P2*) (wt. %) | 0 | 50 | 100 |
| Notched Izod impact strength times 10 (ft-lb/inch) (ASTM D-256) | 7.6 | 13.0 | 11.6 |
| Unnotched Izod impact strength (ft-lb/inch) (ASTM D-4812) | 17 | 21 | 20 |

Surprisingly, polymer composition (E2), while offering an exceptionally high level of strength and stiffness (similar to that provided of PRIMOSPIRE® PR-120 and PRIMOSPIRE® PR-250 control (P1*)—see table 1), further exhibited increased impact resistance, both in terms of notched and unnotched Izod, in substantial progress with (P1*) control [synergistic behavior].

Example 3

Biocompatibility Test Results

The biocompatibility of polyarylene (P2*) was tested using 4 standard tests covering cytotoxicity, sensitization, systemic toxicity and subacute (subchronic toxicity).

ISO Guinea Pig Maximization Sensitization Test Results:

Pellets of polyarylene (P2*) were extracted according to ISO 10993-12. The resulting extracts and control blanks were injected to different guinea pigs. On day 6, the dorsal site was reshaved and sodium lauryl sulfate in mineral oil was applied. On day 7, the animals were topically patched with the appropriate test extract and the corresponding blank animals were patched with the corresponding control blank. The patches were removed after 48±2 hours of exposure. Following a 2 week rest period, the animals were topically patched with the appropriate test extract and the corresponding blank animals were patched with the corresponding control blank. The patches were removed after 24±2 hours of exposure. The dermal patch sites were observed for erythema and edema 24±2 and 48±2 hours of exposure. Each animal was assessed for a sensitization response based upon the dermal scores. None of them elicit a sensitization response.

Minimum Essential Medium Elution Using L-929 Mouse Fibroblast Cells (ISO) (Cytotoxicity) Test Results:

Pellets of polyarylene (P2*) were extracted at 37±1° C. for 24-25 hours. The extract was inoculated onto the cell line and incubated at 37±1° C. in a humidified atmosphere with 5±1% $CO_2$ in the air. Cultures were evaluated for cytotoxic effects by microscopic observations after 24, 48 and 72 hours incubation periods. Polyarylene (P2*) was considered non-toxic.

ISO Intracutaneous Reactivity Test:

Pellets of polyarylene (P2*) were extracted for 72±2 hours at 37±1° C. Two New Zealand white rabbits (*Oryctolagus cuniculus*) each received 5 sequential 0.2 mL intracutaneous injections along either side of the dorsal mid-line with the test extract on one side and the control extract on the other. The irritations reactions were scored at 24, 48 and 72 hours post-injection on each rabbit for evidence of erythema and edema. Polyarylene (P2*) was considered as non-irritant.

ISO Acute Systemic Injection Test

Pellets of polyarylene (P2*) were extracted for 72±2 hours at 37±2° C. Groups of five albino, Swiss mice (*Mus musculus*) were injected systemically with test or control extracts at a dosing of 50 mL per kg body weight. The animals were observed for signs of toxicity immediately after injection and at 4, 24, 48 and 72 hours post injection. Polyarylene (P2*) was considered non-toxic.

The invention claimed is:

1. A prosthetic device comprising at least one part consisting of a material comprising at least one polyarylene (P1) and at least one polyarylene (P2), wherein the efficient arylene recurring units (R1) of the polyarylene (P1) are a mix (M1) consisting of:
    at least 70 mole %, based on the total number of moles of efficient arylene recurring units (R1), of rigid rod-forming arylene units (Ra), said rigid rod-forming arylene units (Ra) being optionally substituted by at least one monovalent substituting group
    with
    from 5 to 30 mole %, based on the total number of moles of efficient arylene recurring units (R1), of kink-forming arylene units (Rb), said kink-forming arylene units being optionally substituted by at least one monovalent substituting group;

and wherein the efficient arylene recurring units (R2) of the polyarylene (P2) are a mix (M2) consisting of:

less than 70 mole %, based on the total number of moles of efficient arylene recurring units (R2), of rigid rod-forming arylene units (Ra), said rigid rod-forming arylene units (Ra) being optionally substituted by at least one monovalent substituting group with more than 30 mole %, up to 90 mole %, based on the total number of moles of efficient arylene recurring units (R2), of kink-forming arylene units (Rb), said kink-forming arylene units being optionally substituted by at least one monovalent substituting group, and further wherein said prosthetic device is:

an orthopaedic prosthesis comprising a manufactured replacement for an end and/or an articulating surface of a bone;

a manufactured replacement for a portion of a bone distant from an articulating surface; or an artificial body part selected from the group consisting of limbs, eyes, and implants.

2. The prosthetic device according to claim 1, wherein the polyarylene (P1) is a kinked rigid-rod polyphenylene copolymer, essentially all, the recurring units of which consist of a mix (M1) of p-phenylene substituted by a phenylketone group with unsubstituted m-phenylene in a mole ratio p-phenylene:m-phenylene of from 79:21 to 95:5, and wherein the polyarylene (P2) is a kinked rigid-rod polyphenylene copolymer, essentially all the recurring units of which consist of a mix (M2) of p-phenylene substituted by a phenylketone group with unsubstituted m-phenylene in a mole ratio p-phenylene:m-phenylene of from 35:65 to 60:40.

3. The prosthetic device according to claim 1, wherein essentially all the recurring units of the polyarylene (P2) are efficient arylene recurring units (R2).

4. The prosthetic device according to claim 1, wherein the weight of the polyarylene (P2), based on the combined weight of the polyarylene (P1) and the polyarylene (P2), is of at least 5% and at most 95%.

5. The prosthetic device according to claim 1, wherein the weight of the polyarylene (P2), based on the combined weight of the polyarylene (P1) and the polyarylene (P2), is of at least 40% and at most 85%.

6. The prosthetic device according to claim 1, wherein the weight of the polyarylene (P2), based on the combined weight of the polyarylene (P1) and the polyarylene (P2), ranges from 40 to 65%.

7. The prosthetic device according to claim 1, wherein the combined weight of the polyarylene (P1) and of the polyarylene (P2), based on the total weight of the material, is above 80%.

8. The prosthetic device according to claim 1, wherein said material consists essentially of the polyarylene (P1) and the polyarylene (P2).

9. The prosthetic device according to claim 1, wherein said prosthetic device is an orthopaedic prosthesis comprising a manufactured replacement for an end and/or an articulating surface of a bone.

10. The prosthetic device according to claim 1, wherein said prosthetic device is a manufactured replacement for a portion of a bone distant from an articulating surface.

11. The prosthetic device according to claim 1, wherein said prosthetic device is an artificial body part.

12. The prosthetic device according to claim 11, wherein said artificial body is selected from the group consisting of limbs, eyes, and implants.

* * * * *